US006285830B1

(12) United States Patent
Basaganas Millan

(10) Patent No.: US 6,285,830 B1
(45) Date of Patent: Sep. 4, 2001

(54) EVAPORATED DEVICE FOR THE EVAPORATION OF VOLATILE PRODUCTS WITH VARIABLE EVAPORATION INTENSITY BY INTERPOSITION OF A MOBILE BRUSHING

(75) Inventor: Jordi Basaganas Millan, Cerdanyola del Valles (ES)

(73) Assignee: DBK Espana, S.A., Cerdanyola del Valles ( * ) Notice: Subject to any disclaimer, the term of this patent is extended or adjusted under 35 U.S.C. 154(b) by 0 days.

(21) Appl. No.: 09/529,819

(22) PCT Filed: Aug. 19, 1999

(86) PCT No.: PCT/ES99/00265

§ 371 Date: Apr. 19, 2000

§ 102(e) Date: Apr. 19, 2000

(87) PCT Pub. No.: WO00/10617

PCT Pub. Date: Mar. 2, 2000

(30) Foreign Application Priority Data

Aug. 21, 1998 (ES) .................................................. 9801793

(51) Int. Cl.⁷ .............................. A61M 16/00; F24F 6/08
(52) U.S. Cl. .................. 392/395; 392/390; 261/DIG. 65
(58) Field of Search ..................................... 392/386, 390, 392/391, 394, 395, 404, 405; 261/142, 99, 100, 101, DIG. 65

(56) References Cited

U.S. PATENT DOCUMENTS 1,994,932 * 3/1935 Vidal ................................... 392/405
5,038,394 * 8/1991 Hasegawa et al. ................... 392/395
5,095,647 * 3/1992 Zobele et al. .......................... 43/125
5,222,186 * 6/1993 Schimanski et al. ................ 392/395
5,647,053 * 7/1997 Schroeder et al. ................... 392/395

FOREIGN PATENT DOCUMENTS

| 297 14 848 U1 | 12/1997 | (DE) . |
| 1 015255 U | 9/1990 | (ES) . |
| 9-308422 | 12/1997 | (JP) . |
| WO 98/19526 | 5/1998 | (WO) . |
| WO 00/10617 | 3/2000 | (WO) . |

OTHER PUBLICATIONS

1995 IEEE International Solid–State Circuits Conference Digest of Technical Papers, pp. 226–227, "A 256 ×256 CMOS Active Pixel Image Sensor with motion Detection", A. Dickinson et al.

1989 "Analog VISI and Neural Systems", Addison Wesley and C. Mead.

* cited by examiner

Primary Examiner—Sang Paik
(74) Attorney, Agent, or Firm—Helfgott & Karas, PC

(57) ABSTRACT

A device is disclosed meant to perform evaporation of insecticides, perfumes or the like, wherein the degree of evaporation is controlled by a moving cap (9) which makes up the regulating element (6), which is meant to produce a chimney effect in the upwards motion of the generated vapor, so that this effect enhances evaporation, while regulation is achieved by the different heights at which moving cap (9) can be placed. This displacement is performed manually by moving guide (13) inside inclined track (10).

6 Claims, 5 Drawing Sheets

EVAPORATED DEVICE FOR THE EVAPORATION OF VOLATILE PRODUCTS WITH VARIABLE EVAPORATION INTENSITY BY INTERPOSITION OF A MOBILE BRUSHING

OBJECT OF THE INVENTION

The present invention relates to a device designed to evaporate volatile products for air fresheners, insecticides or similar substances, by heat provided by electrical resistors, in order to enhance the evaporation of the product which soaks a wick from the product container.

The invention centers on the means which the device incorporates in order to allow an adjustable intensity of evaporation.

BACKGROUND OF THE INVENTION

Volatile substance evaporators are widely known in the market, generally applied to insecticides or perfumes, and having a vessel containing the product to be evaporated, which rises by capillarity through a wick which leads the product near heating resistors which by their heat cause the evaporation.

In order to adapt use of these devices to different utilization conditions or consumer preferences, the rate of evaporation of the substances may be controlled, thus releasing a larger or smaller amount of evaporated product to the surroundings.

In this sense patent application No. 9,701,388 is known, in which one of these devices is disclosed where the rate of evaporation is controlled by changing the relative position of the wick and the heating element.

In this device, the electrical heating resistors are static, and it is the container and the wick which move axially by means of a threading in order to change the degree of exposure of the wick in the area of influence of the heating resistors.

These devices seek to combine simplicity and economy of production with efficiency and ease of use, as well as to make this use attractive to the consumer.

DESCRIPTION OF THE INVENTION

The invention here disclosed has been designed to provide an evaporator for volatile products with adjustable evaporation rate, in which the means which make the evaporation possible imply greater simplicity of construction and an easier and more pleasant operation of the device.

The adjustment of the rate of evaporation is achieved by a moving cap, which ill addition to providing the evaporator with the aforementioned characteristics, allows a more efficient regulation of the evaporation of the volatile product than in previously known systems.

In this way the volatile product evaporator is made from the basic structure for these devices, with a case or body which houses the heating resistors and extemalliy forming a plug for connection to the electrical mains, for power supply to the heating resistances. As a rule these resistors are of the PTC type.

The lower end of the case is provided with means of coupling the vessel containing the volatile product, either by screwing on or by any other conventional technique, so that it may be replaced by a new vessel when the content is exhausted.

Inside the vessel is a cylindrical wick which absorbs the liquid by porosity so that it rises up through it until it is near the heating resistors.

Based on this known arrangement of these devices, the invention is centered in that in order to determine the rate of evaporation, the evaporator is provided with a cap which can be manually axially moved, inside which is housed the wick soaked with the volatile product.

The function of the cap is to create a chimney effect which affects the rise of the vapor generated in the wick, so that this chimney effect increases the rising speed of this vapor, thereby increasing the rate of evaporation.

The axial displacement of this cap determines different heights for it, partially completing the path of the vapor to the outlet orifice. The longer this path the greater the chimney effect in the evaporation and vice versa, with a maximum and minimum position being defined by limiting the cap displacement with stops placed inside the case in a suitable manner.

The cap is connected to an arm which ends in a guide, meant to project out from the case through an inclined groove which defines the displacement of this guide. The user will operate this guide manually, which has a shape adapted to the inclined groove so that it may slide in it in either direction, upwards or downwards, thereby axially displacing the cap and adjusting the rate of evaporation.

DESCRIPTION OF THE DRAWINGS

Further advantages and characteristics of this invention will become apparent from the accompanying drawings, attached to the present descriptive memory as an integral part and where for purposes of illustration only and in a non-limiting way the following is shown.

PREFERRED EMBODIMENT OF THE INVENTION

Figure 1:
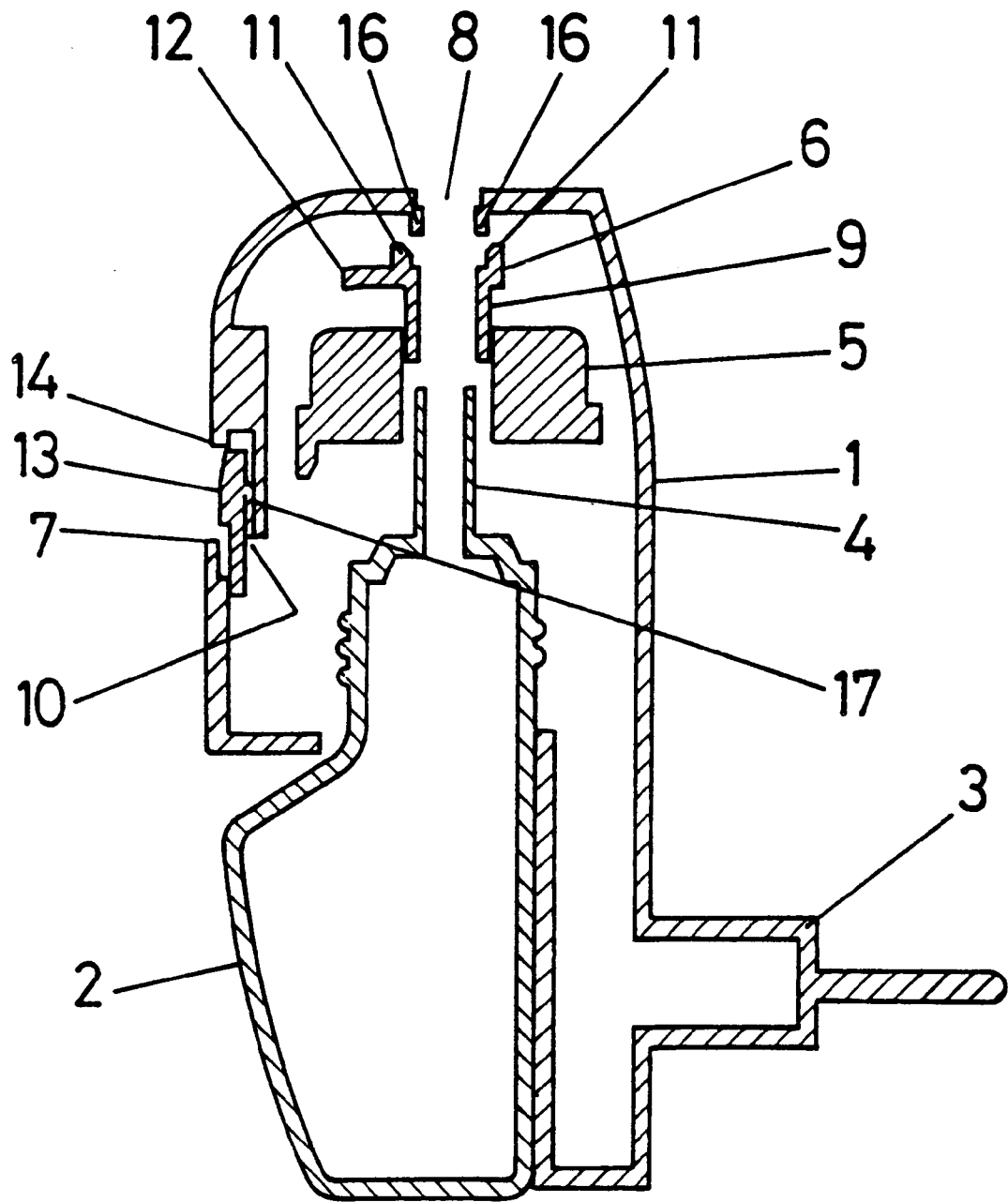
FIG. 1 shows a sectional profile view of the evaporator device with an intermediate position of the movable cap.
Figure 2:
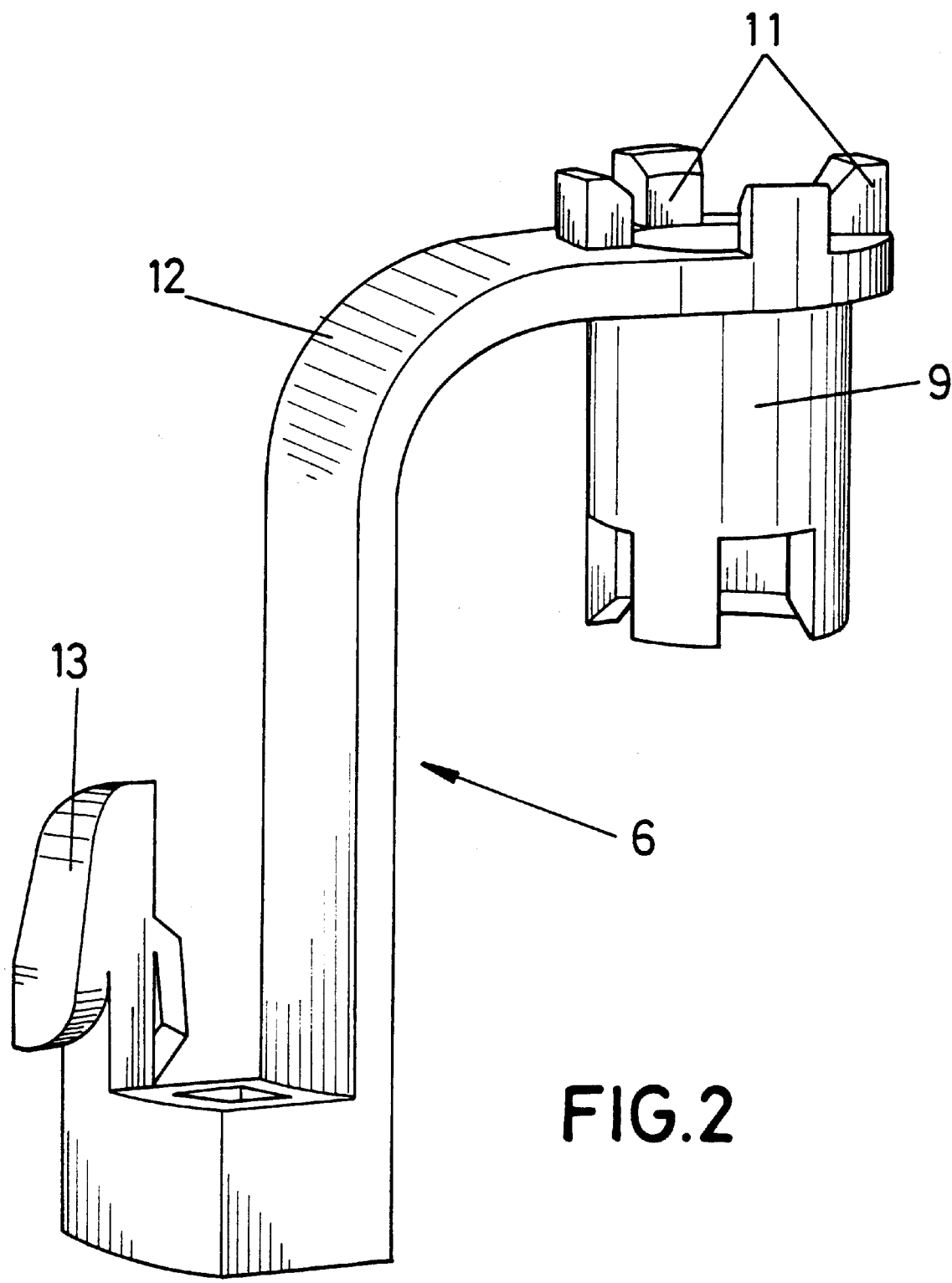
FIG. 2 is a perspective view of the piece which makes up the movable cap.

FIG. 1 shows the elements which together make up the evaporator device, which is based on case (1) which forms a plug (3) for connection to the electrical mains. Within case (1) is housed and anchored heater (5), with PTC type resistors acting as heat generating elements upon connection to the electrical power supply through plug (3).

The lower end of case (1) has an opening for coupling of vessel (2), which contains the volatile product, which rises through wick (4), which in turn passes through an orifice made for this purpose in heater (5) in order to expose the volatile product to the heat generated there.

The vapor produced in this way rises and flows to the outside through orifice (8).

The invention is centered on the inclusion of the regulating element (6) which consists of the movable cap (9) which is placed between wick (4) housed inside it and heater (5) as seen in this FIG. 1, so that it can move axially between the two elements.

The axial displacement is transmitted to the movable cap (9) by arm (12), which is connected to its upper part and which connects it to guide (13) which has its upper and lower extremes inclined and parallel.

In addition, on the front side wall of case (1) is provided an inclined track (10), closed internally by internal wall (17) which forms a window in case (1), as well as forming lower ramp (7) and upper ramp (14). This inclined track (10) houses guide (13) and is shaped to adapt to it, with the inclination of its edges matching that of ramps (7) and (14) on which they will slide, guide (13) being the component on which the user acts in order to regulate the rate of evaporation.

The motion of guide (13) is limited by the internal size of inclined track (10), so that the regulation element (6) is correctly placed at all times, which correct positioning is also aided by the position of movable cap (9) within the cylindrical orifice of the heater (5).

In this way the lateral displacement of guide (13) in either direction and due to its inclination and that of the inclined track (10) has the effect of raising or lowering the regulator element (6) and therefore causing the axial displacement of movable cap (9).

The presence of this movable cap (9) causes a chimney effect in the vapor which is generated, since it creates an upwards channel for the vapor which stops it from spreading to the sides and creating a riding vapor current. As this vapor does not spread to the sides and is channeled it empties the inside of case (1) through orifice (8) more quickly, generating an upwards suction of the air in movable cap (9) which accelerates evaporation.

The different vertical positions for movable cap (9) allow it to create a chimney effect in the entire path of the vapor until it leaves orifice (8) thus establishing a maximum evaporation rate, or to partially complete this path, allowing the vapor to diffuse partially in nearby areas to a greater or lesser degree, thus managing to regulated the rate of evaporation.

Figure 3:
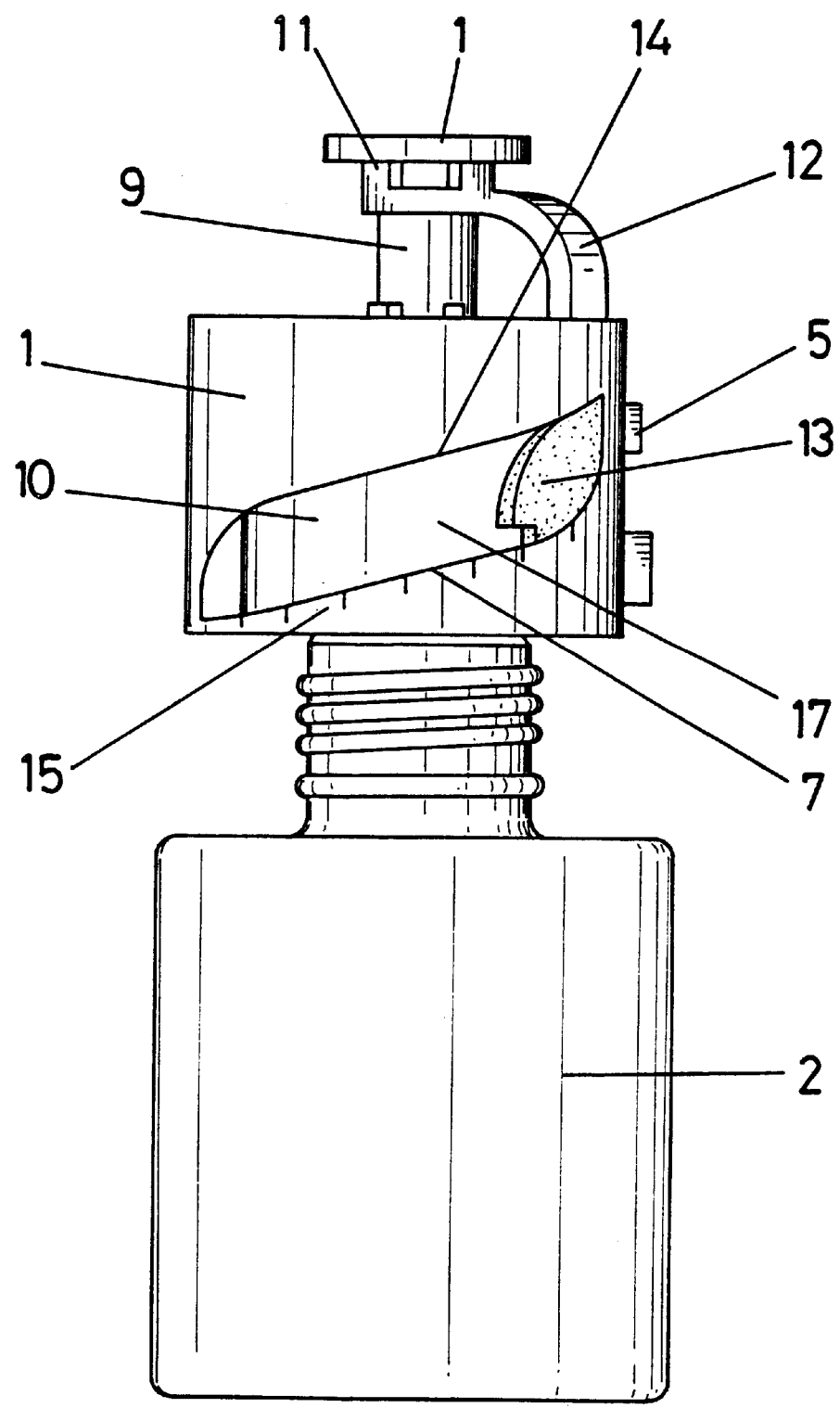
FIG. 3 shows a front elevation of the elements which are part of the invention with the product container vessel coupled and with the cap in its maximum position.
Figure 4:
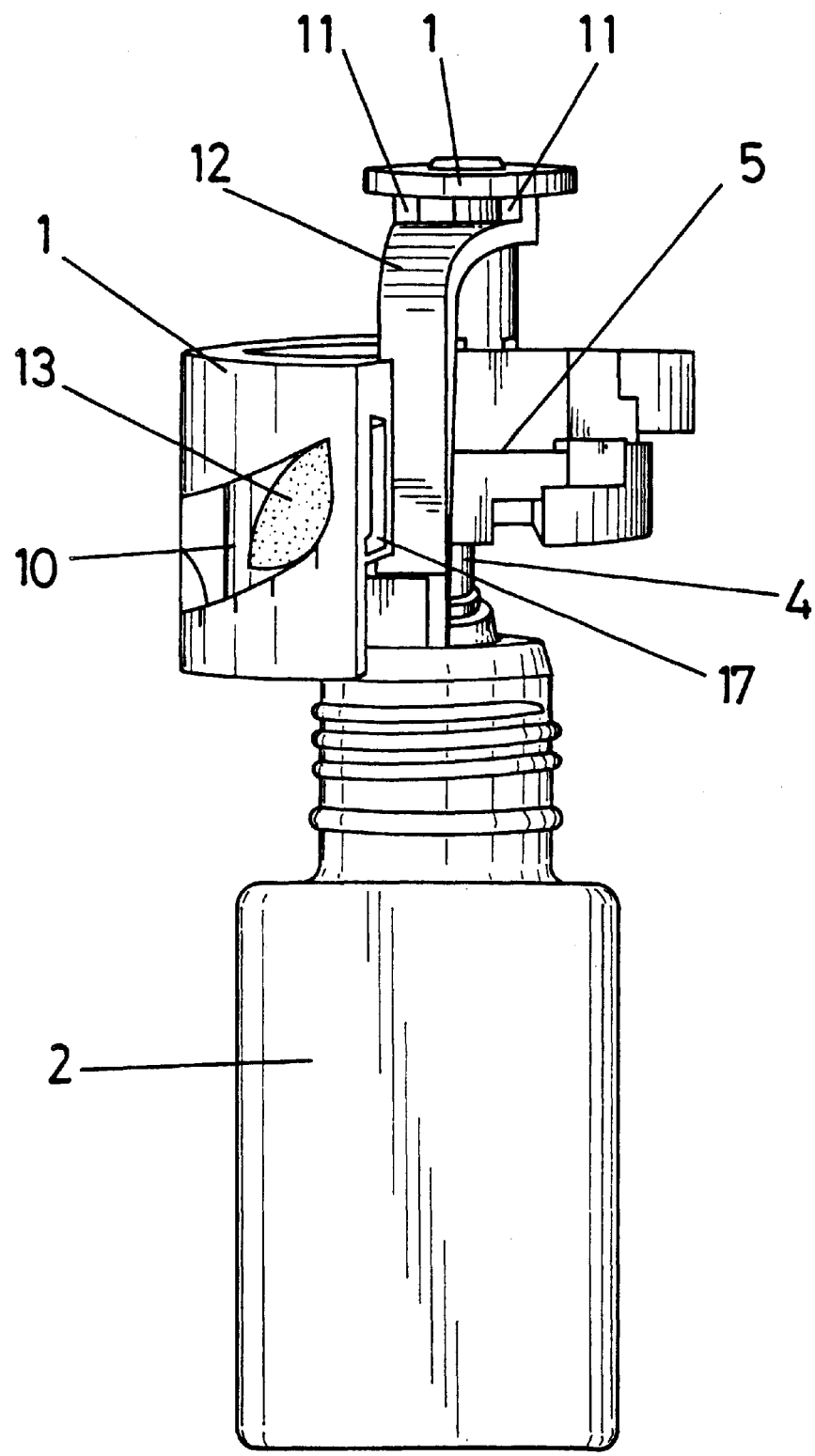
FIG. 4 is a similar view to the previous one seen from a side.

In this preferred embodiment the position of guide (13) which defines the degree of evaporation is the one shown in FIGS. 3 and 4, when it is in the extreme right hand position within inclined track (10), making the movable cap (9) complete the entire path of the vapor.

On the top the regulating element (6) forms battlements (11) which are used as stops for its vertical motion when they hit case (1), as seen in FIGS. 3 and 4. In this maximum position annular wall (16) formed by case (1) is coupled inside battlements (11) to create an extension of the movable cap (9).

Figure 5:
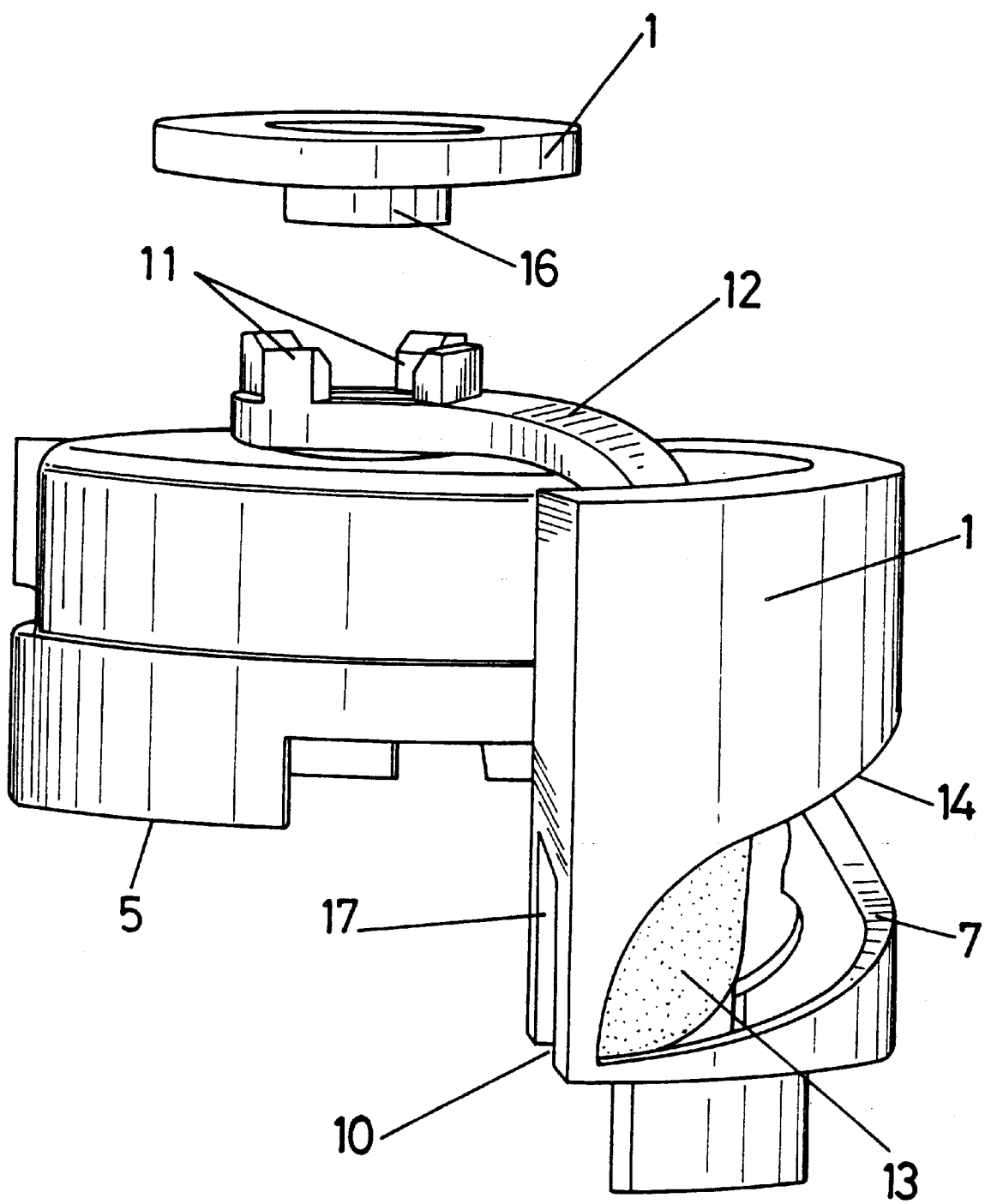
FIG. 5 is a perspective view of the elements which are part of the invention without the container and the wick with the cap in its minimum position.

The position which results in a minimum rate of evaporation is the one shown in FIG. 5, with guide (13) in the leftmost position in inclined track (10), displacement in this direction also being limited by contact with arm (12) on heater (5). In this position as seen in this same figure, the vapor is allowed to spread to the sides, so that the chimney effect is minimal and therefore so is the evaporation, which in this point will be determined by the relative position between wick (4) and heater (5), as well as by their construction.

In addition, in the lowermost position of movable cap (9) it is interposed in the heat transmission between heater (5) and wick (4), thus reducing further the minimum rate of evaporation distancing it from the maximum value. In this way a greater regulation capacity is provided.

So that the user can identify several positions of guide (13), which is to say, rates of evaporation, the invention shall provide a graded scale (15) on the front side wall where inclined track (10) is located, which can consist of any type of marks which determine these positions.

In this preferred embodiment, regulating element (6) is made in plastic, although depending on the application of the evaporating device it can be made in any other material, since it may be interesting for the regulator element (6) to participate in heat transmission between heater (5) and wick (4).

Since the main characteristic of the invention consists of the use of this chimney effect to regulate the extent of evaporation, the invention foresees as an option, that the system with which the axial displacement of movable cap (9) is achieved can be any other which provides the same effect, whether by screwing or any other, with the intervention of different means.

What is claimed is:

1. Evaporator for volatile products wit vapour evaporation rate controlled by means of an interposed moving cap, applicable to the evaporation of insecticides, perfumes or similar, comprising:

a case which forms a plug for electrical power supply, said case having an exit orifice, a heater disposed in said case, said heater baying a heater orifice and an area of influence, a replaceable container for storage of a volatile product and having a wick through which a volatile product rises to reach said area of influence of said heater, and a movable cap interposed between said wick and said heater, said cap being axially movable between said wick and said heater orifice, wherein the regulation of the degree of vapour evaporation is performed by said movable cap, such that said cap defines a conduct for the vapour generated to rise, causing a chimney effect which favours evaporation as it accelerates the upwards flow of the vapour, regulation being obtained by the different positions of said movable cap, so that the rising path of the vapour is completed to a lesser or greater degree until it leaves through said exit orifice, while simultaneously a more efficient evaporation is obtained, and in flat the interposition of said movable cap between said wick and said heater distances the extremes of evaporation, to allow a greater capacity of regulation.

2. Evaporator as in claim 1, wherein said case further comprises a front wall having a track defined by a plurality of inclined ramps, said track being closed by an inner wall, and wherein said evaporator further comprises a regulating element to which said movable cap is connected, said regulating element further comprising an arm having an upper end and a guide having an inclined upper edge and an inclined lower edge, said movable cap being connected to said upper end of said arm and said guide being connected to the other end of said arm, said guide being positionable within said track, and wherein the regulation of the rate of vapour evaporation is controlled by the displacement of said glide within said track, which guide rises or falls on said inclined ramps and which displacement of said guide causes, through said arm, the positioning of said movable cap.

3. Evaporator as in claim 1, wherein said case further comprises a graded scale for identifying several positions of said movable cap, and therefore several evaporation rates.

4. Evaporator as in claim 2, wherein said case further comprises a graded scale for identifying several positions of said guide, and therefore several evaporation rates.

5. Evaporator as in claim 2, wherein said case further comprises an inside having an annular wall, and wherein said regulating element further comprises a lowermost position and an uppermost position and battlements disposed on said upper end of said arm, and wherein said uppermost position is determined by the contact of said battlements with said inside of said case and wherein said lowermost position is determined by the contact between said am and said heater, and wherein said uppermost and lowermost positions of said regulating element are also determined by the position of said guide within said track.

6. Evaporator as in claim 2, wherein said regulator element is plastic.

* * * * *